United States Patent
Moki et al.

(10) Patent No.: US 10,792,352 B2
(45) Date of Patent: Oct. 6, 2020

(54) METHOD FOR REDUCING SKATOLE AND/OR INDOLE IN ANIMALS

(71) Applicant: Boehringer Ingelheim Vetmedica GmbH, Ingelheim am Rhein (DE)

(72) Inventors: Ryouichi Moki, Tokyo (JP); Eigo Sakamoto, Fukuoka (JP); Takeshi Yamaguchi, Koka (JP)

(*) Notice: Subject to any disclaimer, the term of this patent is extended or adjusted under 35 U.S.C. 154(b) by 0 days.

(21) Appl. No.: 16/283,946

(22) Filed: Feb. 25, 2019

(65) Prior Publication Data

US 2019/0358310 A1 Nov. 28, 2019

(30) Foreign Application Priority Data

Feb. 28, 2018 (EP) .................................. 18159151

(51) Int. Cl.
*A61K 39/00* (2006.01)
*A61K 39/02* (2006.01)
*A61K 9/00* (2006.01)

(52) U.S. Cl.
CPC .......... *A61K 39/105* (2013.01); *A61K 9/0053* (2013.01); *A61K 2039/522* (2013.01); *A61K 2039/545* (2013.01); *A61K 2039/552* (2013.01)

(58) Field of Classification Search
CPC .................................................. A61K 39/105
See application file for complete search history.

(56) References Cited

FOREIGN PATENT DOCUMENTS

| WO | 96/39629 A1 | 12/1996 |
|----|-------------|---------|
| WO | 97/20050 A1 | 6/1997 |
| WO | 02/26250 A2 | 4/2002 |
| WO | 2004/084644 A1 | 10/2004 |
| WO | 2005/011731 A1 | 2/2005 |
| WO | 2009/144088 A2 | 12/2009 |

OTHER PUBLICATIONS

Skrlep et al., "Elevated fat skatole levels in immunocastrated, surgically castrated and entire male pigs with acute dysentery," Veterinary Journal, vol. 194, No. 3, Dec. 2012, pp. 417-419.
Visscher et al., "Dietary approaches reducing boar taint-Importance of Lawsonia intracellularis colonisation for interpreting results.", Journal of Animal Physiology and Animal Nutrition, Apr. 1, 2018, vol. 102 Suppl. 1, pp. 3-15.
Xue et al., "Raising intact male pigs for meat: Detecting and preventing boar taint," Swine Health and Production, 1997, vol. 5, No. 4, pp. 151-158.
Masakazu Irie, "Quality and Evaluation for Pork," The Journal of Animal Genetics, 2006, vol. 34, No. 2, pp. 33-44.
Nishioka et al., "Skatole concentration in porcine fat and its influence on sensory evaluation," Nihon Chikusan Gakkaiho, 2011, vol. 82, No. 2, pp. 147-153. with English Abstract.
Hawe et al., "The effects of dietary fibre, lactose and antiobiotic on the levels of skatole and indole in faeces and subcutaneous fat in growing pigs," Animal Science, 1992, vol. 54, No. 3, pp. 413-419.

*Primary Examiner* — Albert M Navarro
(74) *Attorney, Agent, or Firm* — John Ezcurra

(57) ABSTRACT

The present invention relates i.a. to a method for reducing the concentration of skatole and/or indole in an animal comprising administering to said animal an effective amount of an immunogenic composition comprising Lawsonia intracellularis antigen. Therefore, the present invention also relates to methods for reducing pork odor or boar taint.

22 Claims, 1 Drawing Sheet

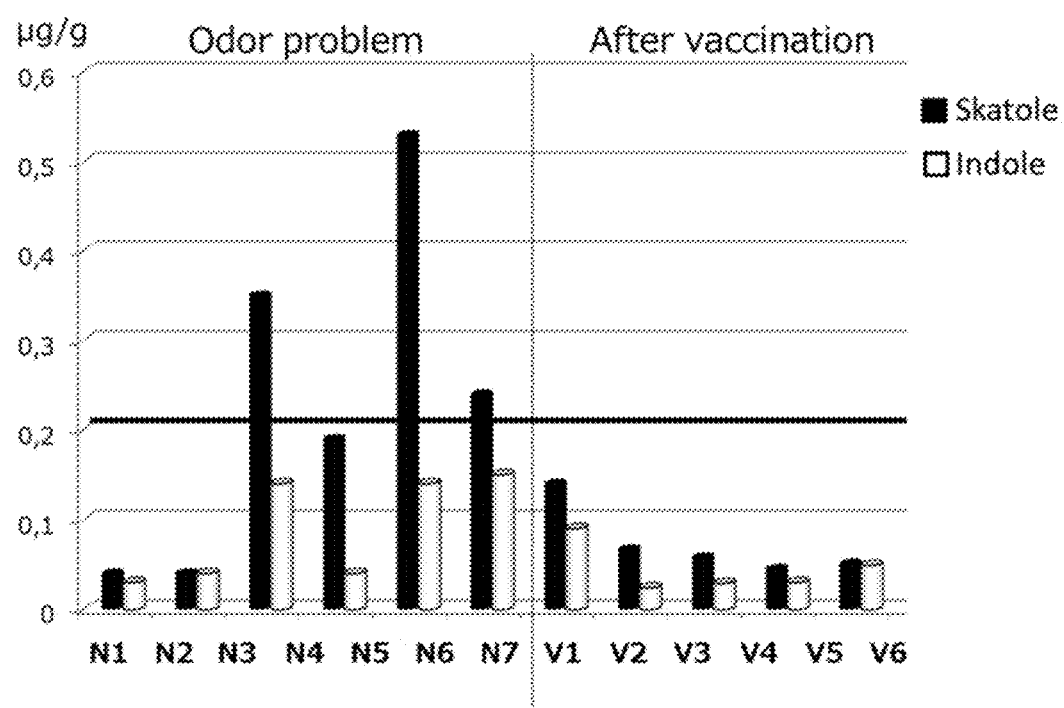

METHOD FOR REDUCING SKATOLE AND/OR INDOLE IN ANIMALS

BACKGROUND

Lawsonia (L.) intracellularis, the causative agent of porcine proliferative enteropathy ("PPE"), affects virtually all animals, including: rabbits, ferrets, hamsters, foxes, horses, and other animals as diverse as ostriches and emus. L. intracellularisis is globally the most prevalent enteric pathogen in swine and is causing significant losses in swine production across the globe.

L. intracellularis vaccines have been approved for use in the United States and Europe (trademark Enterisol®Ileitis) which are based on live attenuated L. intracellularis isolates described in WO96/39629 A1 and WO2005/011731 A1.

Killed L. intracellularis vaccines have been described as well such as in WO2009144088 A2, WO97/20050 A1 and WO2002/26250 A2.

Pork odor is an odor or taste that can be evident during the cooking or eating of pork. There are several compounds important for pork odor, the most important being androstenone, skatole and indole.

Androstenone (a male steroidal pheromone) is produced in the testes of male pigs. Male pigs that are raised for meat production are often castrated shortly after birth to prevent the development of boar taint (pork odor) in the animal.

In contrast, skatole and indole are breakdown products of the tryptophan metabolism in both male and female pigs. Such high concentrations of skatole and indole in fat tissue can give rise to said unpleasant odor or taste.

The amount of skatole stored in adipose tissue depends on several aspects such as the rate of skatole production, intestinal transit time, intestinal absorption and hepatic metabolism. The production of skatole takes place in the intestine by microbial breakdown of the amino acid tryptophan originating from dietary or endogenous protein. Most of the available skatole produced in the intestine is absorbed across the intestinal wall and transported in the blood to the liver, where the majority is degraded. However, the skatole degradation in the liver is hindered by androstenone. The degraded products are then excreted in the urine. The feces only contains minor amounts of skatole. The nondegraded skatole is then deposited in fat and muscle.

The amount of skatole in the animal is influenced by several parameters. The dietary ingredients affect fat concentrations of skatole. Further, other management techniques play a role in skatole production, too. Exemplary, pigs at higher stocking rates have higher fat concentrations of skatole than pigs kept clean at a lower stocking rate.

Skrlep et al 2012 (The Veterinary Journal; 194; pages 417-419) describe that pork odor can even arise in castrated pigs having an intestinal infection. Skrlep et al 2012 studied pigs having an outbreak of acute dysentery caused by Lawsonia intracellularis and *Brachyspira hyodysenteriae* and resulted in cachexia and high mortality.

Importantly, it has been described that diets supplemented with antibiotics (Tylosin or Virginiamycin) or antibiotic feed additives in general do not affect fat concentrations of skatole (Hawe et al. 1992; Anim Prod.; 54: pages 413-419; Hansen et al. 1994; Livest Prod Sci; 39:pages 269-274; Xue et al 1997; JSHAP; 5(4); pages 151-158). Only for one antibiotic (Bacitracin) a decrease of skatole level was observed (Hansen et al. 1997; Animal Science, 64, 351-363). From said studies it is unclear whether the treatment of bacterial infections in the intestine by antibiotics has any or at least a substantial benefit on skatole or indole levels in fat tissue.

Taken together, the skatole or indole levels in fat tissue of pigs is influenced by several parameters such as intestinal absorption of skatole or indole in the intestine, hepatic metabolism, dietary ingredients, stocking rates of pigs, castration of boars, intestinal infections and so forth. However, antibiotic feed in general did not affect fat concentrations of skatole or indole.

Therefore, there is a need for new methods for reducing skatole or indole levels in swine and pork odor in swine, respectively.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art. Generally, the present invention provides a method for reducing the concentration or amount of skatole and/or indole in an animal comprising administering to said animal an effective amount of an immunogenic composition comprising Lawsonia intracellularis antigen.

Further, the present invention provides a method of preventing pork odor in an animal comprising administering to said animal an effective amount of an immunogenic composition comprising Lawsonia intracellularis antigen.

Advantageously, the experimental data provided by the present invention disclose that by the method of the present invention the skatole and/or indole levels in the tissue of pigs can be reduced. Further, by reducing the levels of skatole and/or indole in the tissue of pigs the pork odor or boar taint is reduced.

The term "reducing" means that the concentration or amount of skatole and/or indole is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the concentration of skatole and/or indole. Exemplary, the concentration of skatole and/or indole can be measured by high performance liquid chromatography.

The term "skatole and/or indole" is well known to a person skilled in the art. Skatole is also known as 3-Methylindole. Both, skatole and indole are breakdown products of the tryptophan metabolism in both male and female pigs.

The term amount is used interchangeable with the term concentration.

The term "preventing" generally involves the administration of an effective amount of the immunogenic composition of the present invention to a subject or herd of subjects in need of or that could benefit from such a treatment/prophylaxis. The term "treatment" refers to the administration of the effective amount of the immunogenic composition once the subject or at least some animals of the herd is/are already infected with such Lawsonia intracellularis and wherein such animals already show some clinical signs caused by or associated with such Lawsonia intracellularis infection. The term "prophylaxis" refers to the administration of a subject prior to any infection of such subject with Lawsonia intracellularis or at least where such animal or none of the animals in a group of animals do not show any clinical signs caused by or associated with the infection by such Lawsonia intracellularis. The terms "preventing" and "treatment and/or prophylaxis" are used interchangeable in this application.

The term "in need" or "of need", as used herein means that the administration/treatment is associated with the boosting or improvement in health or clinical signs or any other positive medicinal effect on health of the animals which receive the immunogenic composition in accordance with the present invention.

As used herein, the term "effective amount" means, in the context of a composition, an amount of an immunogenic composition capable of inducing an immune response that reduces the incidence of or lessens the severity of infection or incident of disease in an animal and, thus, reduces the amount of skatole and/or indole in said animal. Such effective amount is able to lessen the incidence of the particular Lawsonia intracellularis infection in a herd or to reduce the severity of clinical signs of the particular Lawsonia intracellularis infection and, thus, reduces the amount of skatole and/or indole in said animal. Particularly, an effective amount refers to TCID50 per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a Lawsonia intracellularis infection. The host is also described as "subject". Preferably, any of the hosts or subjects described or mentioned herein is an animal.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "Lawsonia intracellularis" is known by the person skilled in the art. Lawsonia intracellularis is the causative agent of porcine proliferative enteropathy ("PPE").

An "antigen" as used herein refers to, but is not limited to, components which elicit an immunological response in a host to an immunogenic composition or vaccine of interest comprising such antigen or an immunologically active component thereof. The antigen or immunologically active component may be a whole microorganism (in inactivated or modified live form), or any fragment or fraction thereof, which, if administered to a host, can elicit an immunological response in the host. The antigen may be or may comprise complete live organisms in either its original form or as attenuated organisms in a so called modified live vaccine (MLV). The antigen may further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen may comprise whole organisms inactivated by appropriate methods in a so called killed vaccine (KV). If the organism is a bacterium, the killed vaccine is called a bacterin.

Lawsonia Antigen

In one aspect of the present invention the Lawsonia intracellularis antigen is killed Lawsonia intracellularis or modified live Lawsonia intracellularis.

In one aspect of the present invention the killed Lawsonia intracellularis is a whole cell killed Lawsonia intracellularis.

Killed L. intracellularis vaccines have been described in WO2009144088 A2, WO97/20050 A1 and WO2002/26250 A2.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfate and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the Lawsonia intracellularis. In general, the inaction process is performed until no growth of the Lawsonia intracellularis can be detected in a suitable cultivation system.

Preferably, the inactivated Lawsonia intracellularis are formalin inactivated, preferably using the concentrations as described hereinabove.

Preferred β-Propiolactone inactivation conditions include β-Propiolactone concentration between from about 0.005% (v/v)-4.0% (v/v) and more preferably from about 0.05% (v/v)-2.0% (v/v). Incubation time depends on the resistance of the Lawsonia intracellularis. In general, the inaction process is performed until no growth of the Lawsonia intracellularis can be detected in a suitable cultivation system.

Preferably, the inactivated Lawsonia intracellularis are inactivated by β-Propiolactone, preferably using the concentrations as described hereinabove.

Preferably, the immunogenic composition comprises $10^2$ to $10^{14}$ cells killed Lawsonia intracellularis per dose, more preferably $10^4$ to $10^{12}$ cells killed Lawsonia intracellularis per dose and even more preferably $10^6$ to $10^{10}$ cells killed Lawsonia intracellularis per dose.

Preferably, the immunogenic composition comprises an amount of 25 to 2000 μg killed Lawsonia intracellularis per dose, more preferably an amount of 50 to 1000 μg killed Lawsonia intracellularis per dose and even more preferably an amount of 100 to 800 μg killed Lawsonia intracellularis per dose.

In one aspect of the present invention the immunogenic composition comprises $10^6$ to $10^{10}$ cells killed Lawsonia intracellularis per dose or an amount of 100 to 800 μg killed Lawsonia intracellularis per dose.

In one aspect of the present invention the modified live Lawsonia intracellularis is an avirulent isolate or the Lawsonia intracellularis is attenuated.

The term "attenuated" refers to a pathogen having a reduced virulence. In the present invention "attenuation" is synonymous with "avirulent". In the present invention, an attenuated Lawsonia intracellularis is one in which the virulence has been reduced so that it does not cause clinical signs of a Lawsonia intracellularis infection but is capable of inducing an immune response in the target animal, but may also mean that the clinical signs are reduced in incidence or severity in animals infected with the attenuated Lawsonia intracellularis in comparison with a "control group" of animals infected with non-attenuated Lawsonia intracellularis and not receiving the attenuated bacteria. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group as defined above. Thus, an attenuated, avirulent Lawsonia intracellularis strain or isolate is one that is suitable for incorporation into an immunogenic composition comprising a modified live Lawsonia intracellularis.

Pathogenic and non-pathogenic attenuated bacteria strains of L. intracellularis are well known in state of the art. For example, WO96/39629 and WO05/011731 describe non-pathogenic attenuated strains of L. intracellularis and methods for the preparation thereof.

In particular, WO96/39629 describes the preparation of attenuated bacteria strains of L. intracellularis and the deposited strain ATCC 55783.

WO05/011731 describes the preparation of attenuated bacteria strains of L. intracellularis and the deposited strain PTA-4926.

In one aspect of the present invention the avirulent isolate is PTA-4926 or ATCC 55783.

In one aspect of the present invention the avirulent Lawsonia intracellularis isolate or the attenuated Lawsonia intracellularis is Enterisol®Ileitis.

The recommended dose to be administered to the susceptible animal is preferably about 3.0 TCID50 (tissue culture infective dose 50% end point)/dose to about 9.0 TCID50/dose and more preferably about 4.0 TCID50/dose to about 7.0 TCID50/dose.

In one aspect of the present invention the immunogenic composition comprises about 3.0 to about 9.0 TCID50 of the modified live Lawsonia intracellularis per dose.

In one aspect of the present invention the immunogenic composition comprises about 4.0 to about 7.0 TCID50 of the modified live Lawsonia intracellularis per dose.

Animal

The term "animal" refers preferably to mammals such as mice, rats, guinea pigs, rabbits, hamsters, swine, sheep, dogs, cats, horses, monkeys, or cattle. More preferably, the animal is a swine.

In one aspect of the present invention the animal is a mammal.

In one aspect of the present invention the animal is a pig.

It has to be understood that the term "pig" comprises piglets, sows, gilts, boars and the alike.

In one aspect of the present invention the animal or pig is male or female.

In one aspect of the present invention the animal or pig is male.

In one aspect of the present invention the male animal or pig is castrated or non-castrated.

In one aspect of the present invention the animal is a female pig or castrated male pig.

Intestinal or Lawsonia Infection

In one aspect of the present invention the animal has a gastrointestinal infection.

In one aspect of the present invention the animal has an intestinal infection.

The term "gastrointestinal infection" or "intestinal infection" as used herein refers to a viral, bacterial or parasitic infection in the gastrointestinal tract or intestine of said animal. Said infection may cause clinical or subclinical enteric disease in said animal.

In one aspect of the present invention the animal has an infection with an intestinal pathogen. Preferably, the intestinal pathogen is selected from the list (but not limited to) consisting of: Lawsonia intracellularis, *Brachyspira* spp., pathogenic *Escherichia coli*, *Salmonella* spp., *B. hampsonii* and *B. murdochii*.

In one aspect of the present invention the animal has an infection with Lawsonia intracellularis.

In one aspect of the present invention the animal has an infection with Lawsonia intracellularis and *Brachyspira hyodysenteriae*.

Tissues

In one aspect of the present invention skatole is 3-Methylindole.

In one aspect of the present invention the concentration of skatole and/or indole is reduced in the intestine, fat, muscle, meat or liver tissue.

In one aspect of the present invention the concentration of skatole and/or indole is reduced in the fat, muscle or meat.

In one aspect of the present invention the method reduces pork odor or boar taint.

Pork Odor

The term "pork odor" or "boar taint" as used herein relates to an odor and/or flavor of the pork meat which in general becomes evident during the cooking or eating of said pork meat. Said odor and/or flavor may be to such an extent that the meat is not acceptable for human consumption. Male pigs in general and to a lesser extent female and castrated male pigs also exhibit the phenomena associated with boar taint or pig odor. There are several compounds important for pork odor, the most important being androstenone, skatole and indole. The sensory threshold of skatole in the fat tissue/liquid fat is 0.2 µg/g (see exemplary Skrlep et al 2012 (The Veterinary Journal; 194; pages 417-419)). The sensory threshold of indole in the fat tissue/liquid fat is 0.3 µg/g.

In one aspect of the present invention the method reduces the clinical signs of Lawsonia intracellularis infection.

The term "clinical signs" of Lawsonia intracellularis infection as used herein includes, but is not limited to a reduced average daily weight gain (ADWG), increased variability in weight gain, increased feed conversion ratio, gross lesions in ileum, cecum and colon, diarrhea, detectable bacterial load, shedding of Lawsonia intracellularis or combinations thereof.

Thus, in one aspect of the present invention said method results in an improvement in an efficacy parameter selected from the group consisting of: increased average daily weight gain (ADWG), reduced variability in weight gain, optimized feed conversion ratio, reduced gross lesions in ileum, cecum and colon, reduced diarrhea, reduced bacterial load, reduced shedding of Lawsonia intracellularis, or combinations thereof, in comparison to a non-immunized animal of the same species.

Preferably, clinical signs are reduced in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular Lawsonia intracellularis.

Reduction of Skatole Concentration

In one aspect of the present invention the concentration of skatole is reduced by at least 50% in the fat tissue compared to an animal of a non-vaccinated control group being infected with Lawsonia intracellularis.

In one aspect of the present invention the concentration of skatole is reduced to less than 0.2 µg/g in the fat tissue of animals being infected with Lawsonia intracellularis.

In one aspect of the present invention the concentration of skatole is reduced to less than 0.15 µg/g in the fat tissue of animals being infected with Lawsonia intracellularis.

In one aspect of the present invention the concentration of skatole is reduced to less than 0.1 µg/g in the fat tissue of animals being infected with Lawsonia intracellularis.

In one aspect of the present invention the concentration of skatole is reduced below the sensory threshold in the fat tissue of animals being infected with Lawsonia intracellularis.

Reduction of Indole Concentration

In one aspect of the present invention the concentration of indole is reduced by at least 50% in the fat tissue compared to an animal of a non-vaccinated control group being infected with Lawsonia intracellularis.

In one aspect of the present invention the concentration of indole is reduced to less than 0.3 µg/g in the fat tissue of animals being infected with Lawsonia intracellularis.

In one aspect of the present invention the concentration of indole is reduced to less than 0.15 µg/g in the fat tissue of animals being infected with Lawsonia intracellularis.

In one aspect of the present invention the concentration of indole is reduced to less than 0.05 µg/g in the fat tissue of animals being infected with Lawsonia intracellularis.

In one aspect of the present invention the concentration of indole is reduced below the sensory threshold in the fat tissue of animals being infected with Lawsonia intracellularis.

Age of the Animals

In one aspect of the present invention the immunogenic composition is administered to the animal from an age of three weeks.

In one aspect of the present invention the immunogenic composition is administered to the animal from an age of 10 days.

In one aspect of the present invention the immunogenic composition is administered to the animal from one day of age onwards.

In one aspect of the present invention the immunogenic composition further comprises a veterinary-acceptable carrier.

In one aspect of the present invention the veterinary-acceptable carrier is a diluent.

"Diluent" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In one aspect of the present invention the veterinary-acceptable carrier is a physiologic buffer.

In one aspect of the present invention the pharmaceutically acceptable carrier is phosphate buffered saline.

Preferably, the immunogenic composition further comprises sucrose gelatin stabilizer.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In one aspect of the present invention said veterinary-acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In one aspect of the present invention said veterinary-acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from E. coli (recombinant or otherwise), cholera toxin, IMS 1314, muramyl dipeptide, and combinations thereof.

In one aspect of the present invention said veterinary-acceptable carrier is a water-in-oil-in-water emulsion or a carbomer.

In one aspect of the present invention wherein the immunogenic composition is administered once.

It has furthermore been shown that one dose of the immunogenic composition of the present invention is effective after the administration of such single dose of such immunogenic composition.

In one aspect of the present invention the immunogenic composition is formulated for a single-dose administration.

Preferably, the single-dose has a total volume between about 0.1 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

However, the immunogenic composition can be administered at two or more doses, with a first dose being administered prior to the administration of a second (booster) dose. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

In one aspect of the present invention the immunogenic composition is administered in two doses.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition may be administered by other routes as well. However, most preferred the immunogenic composition is administered intranasal or orally such as by the drinking water or by oral drench.

In one aspect of the present invention wherein the immunogenic composition is administered, intramuscularly, subcutaneously, intranasaly or orally.

In one aspect of the present invention the killed Lawsonia intracellularis is administered intramuscularly or subcutaneously.

In one aspect of the present invention the modified live Lawsonia intracellularis is administered orally or intranasal.

In one aspect of the present invention the immunogenic composition is a vaccine.

DETAILED DESCRIPTION

The invention provides the following embodiments

1. A method for reducing the concentration or amount of skatole and/or indole in an animal comprising administering to said animal an effective amount of an immunogenic composition comprising Lawsonia intracellularis antigen.

2. An immunogenic composition comprising Lawsonia intracellularis antigen for use in a method for reducing the concentration or amount of skatole and/or indole in an animal comprising administering to said animal an effective amount of said immunogenic composition.

3. A method of preventing pork odor in an animal comprising administering to said animal an effective amount of an immunogenic composition comprising Lawsonia intracellularis antigen.

4. An immunogenic composition comprising Lawsonia intracellularis antigen for use in a method of preventing pork odor in an animal comprising administering to said animal an effective amount of said immunogenic composition.

5. The method according to any one of clauses 1 to 4, wherein the Lawsonia intracellularis antigen is killed Lawsonia intracellularis or modified live Lawsonia intracellularis.

6. The method according to clause 5, wherein the killed Lawsonia intracellularis is a whole cell killed Lawsonia intracellularis.

7. The method according to clause 6, wherein the immunogenic composition comprises $10^6$ to $10^{10}$ cells killed Lawsonia intracellularis per dose or an amount of 100 to 800 µg killed Lawsonia intracellularis per dose.

8. The method according to clause 5, wherein the modified live Lawsonia intracellularis is an avirulent isolate or the Lawsonia intracellularis is attenuated.

9. The method according to clause 8, wherein the avirulent isolate is PTA-4926 or ATCC 55783.

10. The method according to clause 8 or 9, wherein the immunogenic composition comprises about 3.0 to about 9.0 TCID50 of the modified live Lawsonia intracellularis per dose.

11. The method according to any one of clauses 8 to 10, wherein the immunogenic composition comprises about 4.0 to about 7.0 TCID50 of the modified live Lawsonia intracellularis per dose.

12. The method according to any one of clauses 1 to 11, wherein the animal is a pig.

13. The method according to any one of clauses 1 to 12, wherein the animal or pig is male or female.

14. The method according to any one of clauses 1 to 13, wherein the animal or pig is male.

15. The method according to clause 14, wherein the male animal or pig is castrated or non-castrated.

16. The method according to any one of clauses 1 to 15, wherein the animal has an intestinal infection.

17. The method according to any one of clauses 1 to 16, wherein the animal has an infection with an intestinal pathogen.

18. The method according to any one of clauses 1 to 17, wherein the animal has an infection with Lawsonia intracellularis or an infection with Lawsonia intracellularis and *Brachyspira hyodysenteriae*.

19. The method according to any one of clauses 1 or 2 or 5 to 18, wherein skatole is 3-Methylindole.

20. The method according to any one of clauses 1 to 19, wherein the concentration of skatole and/or indole is reduced in the intestine, fat, muscle, meat or liver tissue.

21. The method according to any one of clauses 1 to 20, wherein the concentration of skatole and/or indole is reduced in the fat, muscle or meat.

22. The method according to any one of clauses 1 to 21, wherein the method reduces pork odor or boar taint.

23. The method according to any one of clauses 1 to 22, wherein the method reduces the clinical signs of Lawsonia intracellularis infection.

24. The method according to any one of clauses 1 to 23, wherein the concentration of skatole is reduced by at least 50% in the fat tissue compared to an animal of a non-vaccinated control group being infected with Lawsonia intracellularis.

25. The method according to any one of clauses 1 to 24, wherein the concentration of skatole is reduced to less than 0.2 µg/g in the fat tissue of animals being infected with Lawsonia intracellularis.

26. The method according to any one of clauses 1 to 24, wherein the concentration of skatole is reduced to less than 0.15 µg/g in the fat tissue of animals being infected with Lawsonia intracellularis.

27. The method according to any one of clauses 1 to 24, wherein the concentration of skatole is reduced to less than 0.1 µg/g in the fat tissue of animals being infected with Lawsonia intracellularis.

28. The method according to any one of clauses 1 to 27, wherein the concentration of skatole is reduced below the sensory threshold in the fat tissue of animals being infected with Lawsonia intracellularis.

29. The method according to any one of clauses 1 to 28, wherein the concentration of indole is reduced by at least 50% in the fat tissue compared to an animal of a non-vaccinated control group being infected with Lawsonia intracellularis.

30. The method according to any one of clauses 1 to 29, wherein the concentration of indole is reduced to less than 0.3 µg/g in the fat tissue of animals being infected with Lawsonia intracellularis.

31. The method according to any one of clauses 1 to 29, wherein the concentration of indole is reduced to less than 0.15 µg/g in the fat tissue of animals being infected with Lawsonia intracellularis.

32. The method according to any one of clauses 1 to 29, wherein the concentration of indole is reduced to less than 0.05 µg/g in the fat tissue of animals being infected with Lawsonia intracellularis.

33. The method according to any one of clauses 1 to 32, wherein the concentration of indole is reduced below the sensory threshold in the fat tissue of animals being infected with Lawsonia intracellularis.

34. The method according to any one of clauses 1 to 33, wherein the immunogenic composition is administered to the animal from an age of three weeks.

35. The method according to any one of clauses 1 to 34, wherein the immunogenic composition is administered to the animal from an age of 10 days.

36. The method according to any one of clauses 1 to 35, wherein the immunogenic composition is administered to the animal from one day of age onwards.

37. The method according to any one of clauses 1 to 36, wherein the immunogenic composition further comprises a veterinary-acceptable carrier.

38. The method according to clause 37, wherein said veterinary-acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

39. The method according to clause 37 or 38, wherein the veterinary-acceptable carrier is an adjuvant or a physiologic buffer.

40. The method according to any one of clauses 37 to 39, wherein said veterinary-acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymerd, SAF-M, monophosphoryl lipid A, Avridine lipid-amine, heat-labile enterotoxin from E. coli (recombinant or otherwise), cholera toxin, IMS 1314, muramyl dipeptide, and combinations thereof.

41. The method according to any one of clauses 37 to 40, wherein said veterinary-acceptable carrier is a water-in-oil-in-water emulsion or a carbomer.

42. The method according to any one of clauses 1 to 41, wherein the immunogenic composition is administered once.

43. The method according to any one of clauses 1 to 41, wherein the immunogenic composition is administered in two doses.

44. The method according to any one of clauses 1 to 43, wherein the immunogenic composition is administered, intramuscularly, subcutaneously, intranasaly or orally.

45. The method according to any one of clauses 1 to 7 and 12 to 44, wherein the killed Lawsonia intracellularis is administered intramuscularly or subcutaneously.

46. The method according to any one of clauses 1 to 5 and 8 to 44, wherein the modified live Lawsonia intracellularis is administered orally or intranasaly.

47. The method according to any one of clauses 1 to 46, wherein the immunogenic composition is a vaccine.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 illustrates the concentrations of skatole and indole in samples of backfat. N: Non vaccinated during the odor problems, V: Vaccinated.

EXAMPLES

The following examples are only intended to illustrate the present invention. They shall not limit the scope of the claims in any way.

Black tarry diarrhoea and sudden death were observed in late fatteners in a 500-sows farrow-to-finish farm indicated disease caused by Lawsonia intracellularis infection. A hose-like thickening of ileum mucosa covered with pseudomembrane was found at necropsy confirming the clinical diagnosis (data not shown). Further, an infection with Brachyspira hyodysenteriae was diagnosed (data not shown). Furthermore, serum samples were tested for Li (Lawsonia intracellularis) antibodies (bioScreen Ileitis antibody-ELISA) confirming seroconversion at 120 days of age (data not shown). Around the same time, the pork sales destination reported that their customers brought complaints of pork odor. This pork was from the batch having the PHE problems. Seven carcass samples of the batch were submitted to NH Foods Ltd. R&D Center for determination of skatole and indole concentrations in backfat. Skatole concentration was 0.04-0.53 µg/g (average 0.22 µg/g), three samples (42%) exceeded the sensory threshold of 0.2 µg/g (see FIG. 1). Indole concentration was less than sensory threshold of 0.3 µg/g, ranging 0.03-0.15 µg/g (average 0.09 µg/g) (see FIG. 1).

Vaccination with an oral live attenuated Lawsonia intracellularis vaccine (Enterisol® Ileitis, Boehringer Ingelheim) was implemented at 40 days of age according to the instruction of the manufacturer. Five months after implementing vaccination when the vaccinated pigs were marketed, skatole and indole concentrations of backfat were measured using six samples, and Li antibody test was performed again confirming that Li was still present on the farm (data not shown). Average concentrations of skatole and indole were 0.07 µg/g and 0.02 µg/g, respectively, a decrease of 68% and 78% and compared to before vaccination. No samples exceeded sensory threshold (see FIG. 1).

Skatole, by-product of microbial breakdown of tryptophan in the intestine, has strong odor. Nondegraded skatole deposited in fat was elevated. However, vaccination against Li infection improved clinical symptoms as well as pork odor. We hypothesize that infection with Lawsonia intracellularis may led to increased abnormal fermentation or increased intestinal absorption, which caused elevetad skatole production in the intestine.

The invention claimed is:

1. A method for reducing the concentration of skatole and/or indole in a first group of animals in a farm comprising: (i) evaluating whether at least one animal from a second group of animals in said farm has an infection with Lawsonia intracellularis or shows clinical signs associated with a Lawsonia intracellularis infection; and if said at least one animal from said second group of animals is confirmed to have an infection with Lawsonia intracellularis or shows clinical signs associated with a Lawsonia intracellularis infection, (ii) administering to said first group of animals an effective amount of an immunogenic composition comprising Lawsonia intracellularis antigen.

2. A method of preventing pork odor during cooking or eating pork meat from a first group of pigs in a farm comprising: (i) evaluating whether at least one animal from a second group of pigs from said farm has an infection with Lawsonia intracellularis or shows clinical signs associated with a Lawsonia intracellularis infection; and if said at least one animal from said second group of pigs is confirmed to have an infection with Lawsonia intracellularis or shows clinical signs associated with a Lawsonia intracellularis infection, (ii) administering to said first group of pigs an effective amount of an immunogenic composition comprising Lawsonia intracellularis antigen.

3. The method according to claim 1 or 2, wherein the Lawsonia intracellularis antigen is killed Lawsonia intracellularis or modified live Lawsonia intracellularis.

4. The method according to claim 1 or 2, wherein the immunogenic composition comprises $10^6$ to $10^{10}$ cells killed Lawsonia intracellularis per dose or an amount of 100 to 800 µg killed Lawsonia intracellularis per dose.

5. The method according to claim 3, wherein the modified live Lawsonia intracellularis is an avirulent isolate or the Lawsonia intracellularis is attenuated.

6. The method according to claim 3, wherein the immunogenic composition comprises about 3.0 to about 9.0 TCID50 of the modified live Lawsonia intracellularis per dose.

7. The method according to claim 1, wherein the animal is a pig.

8. The method according to claim 1, wherein skatole is 3-Methylindole.

9. The method according to claim 1, wherein the concentration of skatole and/or indole is reduced in the intestine, fat, muscle, meat or liver tissue.

10. The method according to claim 1, wherein the method reduces pork odor or boar taint.

11. The method according to claim 1 or 2, wherein the method reduces the clinical signs of Lawsonia intracellularis infection in the treated animal or treated pig.

12. The method according to claim 1, wherein the concentration of skatole in said first group of animals is reduced by at least 50% in the fat tissue compared to an animal in said second group of animals being infected with Lawsonia intracellularis.

13. The method according to claim 1, wherein the concentration of skatole in animals from said first group of animals is reduced to less than 0.2 µg/g in the fat tissue of the animals.

14. The method according to claim 1, wherein the concentration of skatole in animals from said first group of animals is reduced below the sensory threshold in the fat tissue of the animals.

15. The method according to claim 1, wherein the concentration of indole in animals from said first group of animals is reduced by at least 50% in the fat tissue compared to an animal in said second group of animals being infected with Lawsonia intracellularis.

16. The method according to claim 1, wherein the concentration of indole in animals from said first group of animals is reduced to less than 0.3 µg/g in the fat tissue of the animals.

17. The method according to claim 1, wherein the concentration of indole in animals from said first group of animals is reduced below the sensory threshold in the fat tissue of the animals.

18. The method according to claim 1 or 2, wherein the immunogenic composition is administered to the animal or pig from one day of age onwards.

19. The method according to claim 1 or 2, wherein the immunogenic composition further comprises a veterinary-acceptable carrier.

20. The method according to claim 1 or 2, wherein the immunogenic composition is administered once or in two doses.

21. The method according to claim 1 or 2, wherein the immunogenic composition is administered, intramuscularly, subcutaneously, intranasally or orally.

22. The method according to claim 1 or 2, wherein the immunogenic composition is a vaccine.

* * * * *